United States Patent
Peyman et al.

(10) Patent No.: US 6,878,547 B1
(45) Date of Patent: Apr. 12, 2005

(54) ANTISENSE OLIGONUCLEOTIDES AGAINST TENASCIN FOR TREATING VITILIGO

(75) Inventors: Anuschirwan Peyman, Kelkheim (DE); Eugen Uhlmann, Glashütten (DE); Caroline Weiser, Hattersheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/554,267

(22) PCT Filed: Oct. 29, 1998

(86) PCT No.: PCT/EP98/06868

§ 371 (c)(1), (2), (4) Date: Jul. 24, 2000

(87) PCT Pub. No.: WO99/25819

PCT Pub. Date: May 27, 1999

(30) Foreign Application Priority Data

Nov. 15, 1997 (DE) .......................................... 197 50 702

(51) Int. Cl.[7] .......................... C12N 15/63; C12Q 1/68; C12P 19/34; C07H 21/02; C07H 21/04
(52) U.S. Cl. .......................... 435/455; 435/6; 435/91.1; 435/91.5; 536/23.1; 536/24.31; 536/24.5
(58) Field of Search ........................ 435/6, 91.1, 91.31, 435/91.5, 455, 375; 536/23.1, 24.5, 24.32, 25.3, 24.31; 514/44

(56) References Cited

U.S. PATENT DOCUMENTS

| 5,217,867 A | * | 6/1993 | Evans et al. .................. 435/7.1 |
| 5,594,122 A | * | 1/1997 | Friesen ....................... 536/24.5 |
| 5,801,154 A | * | 9/1998 | Baracchini et al. ............ 514/44 |
| 6,013,639 A | | 1/2000 | Peyman et al. ............... 514/44 |

FOREIGN PATENT DOCUMENTS

| EP | 0-564801 A1 | * | 2/1993 |
| WO | WO-9421664 | * | 3/1993 |
| WO | WO 94/21664 | | 9/1994 |

OTHER PUBLICATIONS

Robert L. Cleek, Inhibition of smooth muscle cell growth in vitro by an antisense oligodeoxynucleotide released from poly(DL–lactic–co–glycolic acid) microparticles, Journal of Boimedical Materials Research, vol. 35, (1997) pp. 525–530.*
W. James, Towards gene–inhibition therapy; a review of progress and prospects in the field of antiviral antisense nucleic acids and ribozymes. Antiviral Chemistry & Chemotherapy (1991) 2(4) pp 191–214.*
Natalie Milner et al., Selecting effective antisense reagents on combinatorial oligonucleotide arrays, Nature Biotechnology vol. 15, Jun. 1997 pp 537–541.*
Stanley T Crooke. Antisense Research and Application, pp 1–50.*
Andrea D. Branch, A good antisense molecule is hard to find. TIBS 23—Feb. 1998 pp. 45–50.*
Karen Pihl–Carey, Isis To Reconstruct As Crohn's Disease Drug Fails In Phase III, Bioworld Today, Vol. 10, No. 239, pp.1–2.*
Giorgio Palu'In pursuit of new developments for gene therapy of human diseases, Journal of Biotechnology 68 (1999) pp. 1–13.*
Robert L. Cleek, Polymeric Delivery of Inhibitors of Smooth Muscle Cell Proliferation (Restenosis). vol. 59/03–B of Dissertation Abstracts International, p. 1227 93 pages.*
"Cancer Drugs in Clinical Development ISIS 3521" www.i-sip.com/products/3521gi.htm, Oct. 16, 2001.
"Cancer Drugs in Clinical Development ISIS 5132" www.i-sip.com/products/5132gi.htm, Oct. 16, 2001.
"Drug Approvals for Aug. 1998" www.fda.gov/cder/da/da0898.htm, Oct. 16, 2001.
"ISIS 2922" www.aegis.org/pubs/drugs/78.htm, Oct. 16, 2001.
Woolf, T.M., et al., "Specificity of antisense oligonucleotides in vivo." Proc. Natl. Acad. Sci., USA, vol. 89, pp. 7305–7309 (1992).
Peyman, A., et al., "Minimally modified oligonucleotides—combination of end–capping and pyrimidine–protection," Biol. Chem. Hoppe–Seyler, vol. 377, pp. 67–70 (1996).
Le Poole, I.C., et al., "Tenascin is overexpressed in vitiligo lesional skin and inhibits melanocyte adhesion," British Journal of Dermatology, vol. 137, No. 2, pp. 171–178 (1997).
O'Donnell, D.B., et al., "Tenascin is abundant in the skin of vitiligo patients," J. Invest. Dermatol., vol. 98, No. 4, p. 620, Abstract 409 (1992).
Torrence, P.F., et al., "Targeting RNA for degradation with a (2'–5')oligoadenylate–antisense chimera." Proc. Natl. Acad. Sci., USA, vol. 90, pp. 1300–1304 (1993).
Ortigao, J.F.R., et al., "Antisense effect of oligodeoxynucleotides with inverted terminal internucleotidic linkages: a minimal modification protecting against nucleotide degradation," Antisense Research and Dev., vol. 2, pp. 129–146 (1992).

* cited by examiner

Primary Examiner—John L. LeGuyader
Assistant Examiner—Jane Zara

(57) ABSTRACT

The invention relates to specific, optionally modified oligonucleotides with a length of up to 17 nucleotides. Said oligonucleotides correspond to segments of tenascin-coding sequences or can bind to these sequences. The invention also relates to the production and use of the oligonucleotides, for example for the specific inhibition of the expression of tenascin and for producing medicaments used to treat vitiligo.

23 Claims, No Drawings

ANTISENSE OLIGONUCLEOTIDES AGAINST TENASCIN FOR TREATING VITILIGO

This is a § 371 of PCT/EP98/06868, which claims benefit of priority of DE 197 50 702.6 filed Nov. 15, 1997.

The invention relates to specific, optionally modified oligonucleotides having a length of up to 18 nucleotides, preferably a length of 7–15 nucleotides, which corresponds to sections of tenasin-coding sequences and can bind to these sequences, to their preparation and to the use thereof, for example for the specific inhibition of the expression of tenascin and for the production of medicaments which can be used for the treatment of vitiligo.

Vitiligo is understood as meaning an acquired lack of melanocytes, by means of which hypopigmented areas of skin result, which as a rule are sharply demarcated and often symmetrically arranged, form one or two spots or cover almost the entire skin. The hair in hypopigmented regions is normally white and appears white even in the Wood light. The affected skin sites are susceptible to sunburn. The cause of the disorder is unknown. Although vitiligo is considered as a disease which is acquired in the course of life, a familial cluster is occasionally found (autosomally dominant, with incomplete penetrance and variable pronouncement). It can also follow an unusual physical trauma, in particular a skull injury. The association of vitiligo with Addison's disease, diabetes mellitus, pernicious anemia or thyroid gland dysfunction and the increases occurrence of antibodies against throglobulin, cells of the adrenal gland and border cells of the stomach in the serum have led to an immunological or neurochemical cause being suspected. Antibodies against melanin were found in some patients.

All available therapeutic methods lead to satisfactory therapeutic results in only some of the patients (F. Wach et al. H+G 71 (1996) 206). The present therapies (S. P. W. Kumarasinghe, Ceylon Medical Journal 40 (1995) 94) include photochemotherapies (PUVA) for example with methoxypsoralen, phenylalanin or khellin, the transplantation of cultured melanocytes, epidermal grafting, and treatment with steroids or placenta extracts. Recently, treatment with pseudocatalase was reported (Schallreuter et al., Dermatology 190 (1995) 223). Small foci can also be covered with cosmetic make-up or tannic acid solutions.

Poole et al. (British Journal of Dermatol. 137 (1997)171) were able to show that the vitiligo-affected skin has a high content of tenascin in comparison with normal skin. The high tenascin content can contribute to the loss of pigmentation and prevent repigmentation. Tenascin (Crossin, J. Cell. Biol. 61 (1996) 592) is an extracellular matrix glycoprotein, which consists of six identical subunits which are linked to the amino terminus via disulfide bridges. The tenascin subunits have a characteristic domain structure: a cysteine-rich sequence at the amino-terminal end is followed by three sequence sections, in each case constructed of repeating units, made of units homologous to EGF, of units homologous to fibronectin (type III) and of units homologous to fibrinogen.

A number of isoforms of the tenascin subunits exists (designated below as tenascin isoforms), which differ in the number of repeating units which are homologous to fibronectin type III. These isoforms are formed by alternative splicing of the tenascin pre-mRNA and subsequent translation of the various splice variants (a. Leprini et al., Perspectives in Developmental Neurobiology 2 (1994) 117–123). A cDNA from human tension was described (sequence in Table 1) by A. Siri et al. (Nucl. Acids Res. 19 (1991) 525–531). This cDNA is stored under the accession number X56160 in gene databases and can be obtained under this number, for example under EMBL/Genbank/DDBJ/NBRF-PIR. This cDNA contains a sequence section which codes for 12 repeating units which are homologous to fibrinogen type III. The cDNAs of the other isoforms of human tenascin are truncated in this sequence section and code for less than 12 of these repeating units.

The expression of tenascin is limited spatially and temporally and a significance is ascribed to it during the development of an organism and in pathological changes (Crossin, vide supra). Such pathological changes are, for example, vitiligo, tumors and inflammation.

Antisense oligonucleotides offer one possibility for the regulation of gene expression (E. Uhlmann and A. Peyman, Chemical Reviews 90, 543 (1990); S. Agrawal. TIBTECH 1996, 376). WO 94/21664 (L. Denner et al.) describes antisense oligonucleotides against tenascin, which are employed for the inhibition of the proliferation of the smooth cell musculature. The oligonucleotides described there have a length of at least 18 nucleotides. It was an object of the present invention to make available novel oligonucleotides which have advantageous properties and which can be used for the complete and/or partial inhibition of the gene expression of tenascin.

It has surprisingly been found that oligonucleotides which have a length of up to 18 nucleotides can effectively influence the expression of tenascin. The present invention relates to oligonucleotides having 7–17 nucleotide units which are optionally modified. In particular embodiments of the invention, the oligonucleotide has a length of 17, 16, 15, 14, 13, 12, 11, 10, 9, 8 or 7 nucleotides. The oligonucleotide corresponds to sections of tenascin-coding sequences (i.e. the oligonucleotide has a sequence which is complementary to the corresponding section of a tenascin-coding sequence) and the oligonucleotide binds specifically to this tenascin-coding sequence (nucleic acid), for example to the tenascin gene and/or tenascin mRNA and/or tenascin cDNA, the tenascin-coding sequence preferably being of human origin (e.g. human tenascin gene, human tenascin mRNA, human tenascin cDNA). The section of the tenascin-coding sequence which corresponds to the oligonucleotide or is complementary to the oligonucleotide preferably has a length of 17, 16, 15, 14, 13, 12, 11, 10, 9, 8 or 7 nucleotide units (this applies in particular to the determination of the length of a modified and/or chimeric oligonucleotide or of oligonucleotide analogs).

A particular embodiment of the invention relates to an oligonucleotide which binds to a nucleic acid which codes for one of the isoforms of human tenascin or parts thereof and inhibits its expression, where the oligonucleotide has a length of 7 to 15 nucleotides and can optionally be modified, and the physiologically tolerable salts of the oligonucleotide.

A particular embodiment of the invention relates to an oligonucleotide which is directed against one or more specific regions of a tenascin-coding sequence, for example the translation start, the 5'-nontranslated region, the coding region and/or the 3'-noncoding region. In a particular embodiment of the invention, the oligonucleotide can also be directed against one or more regions of a tenascin-coding sequence which codes, for example, for certain domains of the tenascin, for example against the cysteine-rich domain, against a domain homologous to EGF, against a domain homologous to fibronectin type III and/or against a domain homologous to fibrinogen.

One embodiment of the invention relates to an oligonucleotide which binds to a nucleic acid which codes for one of the isoforms of human tenascin or parts thereof and inhibits its expression, where the oligonucleotide can bind to a region of the nucleic acid which comprises a) a part of the 5'-noncoding region and/or the translation start or b) the translation start and/or a part of the coding region or c) a part of the coding region and/or a part of the 3'-noncoding region.

The invention relates to particular to an oligonucleotide which corresponds to a sequence section of the human cDNA according to SEQ ID NO. 1 (Table 1). The invention furthermore relates to an oligonucleotide which corresponds to a sequence section of the cDNA which is stored in gene databases under the accession number X56160.

In specific embodiments of the invention, an oligonucleotide can have, for example, one of the following sequences or parts thereof:

SEQ ID NO.2: 3'-GGTTTGGGTGGAGGTGG-5'
SEQ ID NO.3: 3'-GGAGGTGGTACCCCCGG-5'
SEQ ID NO.4: 3'-GGTGGTACCCCCGG-4'
SEQ ID NO.5: 3'-GGAGGTGGTACCCC-5'
SEQ ID NO.6: 3'-AGAAAGAACGAAAGGAA-5'
SEQ ID NO.7: 3'-GGAGGTGGTACC-5'
SEQ ID NO.8: 3'-GGAGCGATGGCTTCCA-5'
SEQ ID NO.9: 3'-AAAGGAACGGGAGCG-5'
SEQ ID NO.10: 3'-GGTCGGTTTGGGTGG-5'
SEQ ID NO.11: 3'-CTTACAGGTCCGTTGA-5'
SEQ ID NO.12: 3'-GGCCGTGTTCGCTGT-5'
SEQ ID NO.13: 3'-TCACCCCTCTTTCTGG-5'
SEQ ID NO.14: 3'-GGACACCGACACGG-5'
SEQ ID NO.15: 3'-AACGGGAGCGATGG-5'
SEQ ID NO.16: 3'-ATCTCGGGGTCGTC-5'
SEQ ID NO.17: 3'-AAAGAACGAAAGGAA-5'
SEQ ID NO.18: 3'-GGTGGTACCCC-5'
SEQ ID NO.19: 3'-CCCGGTACTGA-5' and
SEQ ID NO.20: 3'-CCACAGAAAGAAC-5'.

The sequences SEQ ID NO. 2 to SEQ ID NO. 20 correspond to sections of the tenascin-coding cDNA, as is shown in Table 1. An oligonucleotide which has one of the sequences SEQ ID NO. 2 to SEQ ID NO.20 is complementary to a corresponding section of a tenascin-coding nucleic acid, e.g. a human tenascin cDNA, and can bind to this nucleic acid. Sequences SEQ ID NO. 3, SEQ ID NO. 4, SEQ ID NO. 5, SEQ ID NO. 7 and SEQ ID NO. 18 are examples of oligonucleotides which have a sequence which is directed against the translation start of the tenascin-coding sequences.

The invention also relates to derivatives of an oligonucleotide, for example its salts, in particular its physiologically tolerable salts. Physiologically tolerable salts are understood as meaning compounds which are readily soluble, soluble or poorly soluble in water, for example according to the definition in the "Deutsches Arzneibuch" [German Pharmacopeia] (9th Edition 1986, official edition, Deutscher Apotheker Verlag Stuttgart), page 19. A specific embodiment of the invention relates to the sodium salt of the oligonucleotide according to the invention. Derivatives are also modified oligonucleotides.

An oligonucleotide can be synthesized completely or partially from the natural nucleotides adenosine phosphate, guanosine phosphate, inosine phosphate, cytidine phosphate, uridine phosphate and thymidine phosphate. One embodiment of the invention relates to an oligonucleotide which is synthesized from the natural nucleotides adenosine, guanosine, inosine, cytidine, uridine and thymidine and in which the nucleosides are linked to one another via phosphoric acid diester internucleoside bridges ("phosphoric acid diester bridges").

In other embodiments of the invention, an oligonucleotide can optionally contain one or more modifications, for example chemical modifications. An oligonucleotide can have a number of identical and/or different modifications. Modifications can be localized on certain nucleotide positions (nucleobase and/or β-D-2'-deoxyribose unit) and/or certain internucleoside bridges.

Examples of chemical modifications are known to the person skilled in the art and are described, for example, in E. Uhlmann and A. Peyman, Chemical Reviews 90 (1990) 543 and "Protocols for Oligonucleotides and Analogs" Synthesis and Properties & Synthesis and Analytical Techniques, S. Agrawal, Ed. Humana Press, Totowa, USA 1993, S. T. Crooke, F. Bennet, Ann. Rev. Pharmacol. Toxicol. 36 (1996) 107–129 and J. Hunziber and C. Leumann (1995) Mod. Synt. Methods, 7, 331–417.

The chemical modification of an oligonucleotide can mean, for example, a) the complete or partial replacement of the phosphoric acid diester bridges (internucleoside bridges) by modified phospho bridges, phosphorothioate, phosphorodithioate, $NR^1R^{1'}$-phosphoramidate, boranophosphate, phosphate-($C_1$–$C_{21}$)-O-alkyl ester, phosphate-[($C_6$–$C_{12}$)-aryl-($C_1$–$C_{21}$)-O-alkyl] ester, ($C_1$–$C_8$)alkylphosphonate and/or ($C_6$–$C_{12}$)-arylphosphonate bridges being examples of modified phospho bridges, where $R^1$ and $R^{1'}$ independently of one another are hydrogen, ($C_1$–$C_{18}$)-alkyl, ($C_6$–$C_{20}$)-aryl, ($C_6$–$C_{14}$)-aryl-($C_1$–$C_8$)-alkyl, preferably hydrogen, ($C_1$–$C_8$)-alkyl and/or methoxyethyl, particularly preferably hydrogen, ($C_1$–$C_4$)-alkyl and/or methoxyethyl or $R^1$ and $R^{1'}$, together with the nitrogen atom carrying them, form a 5- to 6-membered heterocyclic ring, which can additionally contain a further heteroatom from the group consisting of O, S and N; and/or b) the complete or partial replacement of the 3'and/or 5' phosphoric acid diester internucleoside bridges ("phosphoric acid diester bridges") by "dephospho" bridges (described, for example, in Uhlmann, E. and Peyman, A. in "Methods in Molecular Biology", Vol. 20, "Protocols for Oligonukleotides and Analogs", S. Agrawal, Ed., Humana Press, Totowa 1993, Chapter 16, 355ff), formacetal, 3'-thioformacetal, methylhydroxylamine, oxime, methylenedimethylhydrazo, dimethylenesulfone and/or silyl groups being examples of dephospho bridges; and/or c) the complete or partial replacement of the sugar phosphate backbone (replacement of sugar phosphate units) by other units, the other unit being suitable, for example, to synthesize a "morpholine derivative" oligomer (described, for example, in E. P. Stirchak et al., Nucleic Acids Res. 17 (1989) 6129) (i.e. replacement by a morpholino derivative unit) and/or being suitable to synthesize a polyamide nucleic acid ("PNA") described, for example, in P. E. Nielsen et al., Bioconj. Chem. 5 (1994) 3 (EP 0 672 677) (i.e., replacement of a PNA unit, for example 2-aminoethylglycine) and/or being suitable to synthesize a phosphomonoacid ester nucleic acid ("PHONA", "PMENA") (described, for example, in Peyman et al., Angew. Chem. Int. Ed. Engl. 35 (1996) 2632–2638, EP 0 639 898) (i.e. replacement by a PHONA unit); and/or d) the complete or partial replacement of the β-D-2'-deoxyribose (β-D-2'-deoxyribose unit) by modified sugar units, α-D-2'-deoxyribose, L-2'-deoxyribose, 2'-F-2'-deoxyribose, 2'-O-($C_1$–$C_6$)alkylribose, preferably 2'-O-methylribose, 2'-O-($C_2$–$C_6$alkenylribose, 2'-[O-($C_1$–$C_6$) alkyl-O-($C_1$–$C_6$alkyl)-ribose, 2'-$NH_2$-2'-deoxyribose, β-D-xylofuranose, α-arabinofuranose, 2,4-dideoxy-β-D-erythrohexopyranose, carbocyclic sugar analogs (described, for example, in Froehler, J. Am. Chem. Soc. 114 (1992) 8320), open-chain sugar analogs (described, for example, in Vandendriessche et al., Tetrahedron 49 (1993) 7223) and bicyclo sugar analogs (described, for analogs (described, for example, in M. Tarkov et al., Helv. Chim. Acta 76 (1993) 481) being examples of modified sugar units; and/or e) the modification or the complete or partial replacement of the natural nucleoside bases by modified (nucleoside) bases ("nucleobases"), 5-(hydroxymethyl) uracil, 5-aminouracil, pseudouracil, dihydrouracil, 5-($C_1$–$C_6$-alkyluracil, 5-($C_2$–$C_6$)-alkenyluracil, 5-($C_2$–$C_6$)alkynyluracil, 5-($C_1$–$C_6$)alkylcytosine, 5-($C_2$–$C_6$)alkenylcytosine, 5-(C2–C6)alkynylcytosine, 5-fluorouracil, 5-fluorocytosine, 5-chlorouracil, 5-chlorocytosine, 5-bromouracil, 5-bromocytosine, 7-deaza-7-substituted purines, 7-deaza-8-substituted purines, 8-azapurines, 2,4-diaminopurines, 5-bromocytosine, 5-bromouracil, 5-chlorocytosine, 5-chlorouracil, 5-fluorocytosine, 5-fluorouracil, hypoxanthine and uracil being examples of modified bases; and/or f) the conjugation to one or more molecules (oligonucleotide conjugates) which adapt the property (ies) of the oligonucleotide to specific requirements of favorably influence the properties (e.g., cell penetration, nuclease stability, affinity for the tenascin-coding target sequence, pharmacokinetics) of the oligonucleotide (e.g. antisense oligonucleotide, tripe helix-forming oligonucleotide) and/or in the hybridization of the oligonucleotide on the target sequence can attack this with binding and/or crosslinking, polylysine, intercalators such as pyrene, acridine, phenazine, phenanthridine, fluorescent compounds such as fluorescein, crosslinkers such as psoralen, azidoproflavine, lipophilic molecules such as ($C_{12}$–$C_{20}$)alkyl, lipids such as 1,2-dihexadecyl-rac-glycerol, steroids such as cholesterol, testosterone, vitamins such as vitamin E, poly- or oligoethylene glycol, ($C_{12}$–$C_{18}$)alkyl phosphate diesters and —O—$CH_2$—CH(OH)—O—($C_{12}$–$C_{18}$)-alkyl being examples of molecules which can be conjugated to an oligonucleotide, where such molecules can be conjugated to the oligonucleotide at the 5' and/or at the 3' end and/or within the sequence, e.g. via a nucleobase;

g) the conjugation to a 2'5'-linked oligoadenylate or a derivative thereof, a 2'5'-linked triadenylate, a 2'5'-linked tetraadenylate, a 2'5'-linked pentaadenylate etc. being examples of 2'5'-linked oligoadenylates and cordycepin (2'5'-linked 3'-deoxyadenylate) being an example of a derivative of a 2'5'-linked oligoadenylate, the conjugation preferably taking place via a linker, where the 5'-end of the 2'5'-linked oligoadenylate can preferably be a phosphate, diphosphate or triphosphate group, where the linker, for example, can be an oligoethylene glycol, triethylene glycol, tetraethylene glycol and hexaethylene glycol being examples of oligoethylene glycol linkers; and/or h) the introduction of a 3'—3' and/or 5'—5' inversion at the 3' and/or at the 5' end of the oligonucleotide, this type of chemical modification being known to the person skilled in the art and being described, for example, in M. Koga et al., J. Org. Chem. 56 (1991) 3757.

In preferred embodiments of the invention, the oligonucleotide has one or more chemical modifications which independently of one another are selected from a) the complete or partial replacement of the phosphoric acid diester bridges by phosphorothioate and/or ($C_1$–$C_8$)alkylphosphonate bridges, b) the complete or partial replacement of the sugar phosphate backbone by PNA units and/or PHONA units, c) the complete or partial replacement of the β-D-2'-deoxyribose units by 2'-F-2'-deoxyribose, 2'-O-($C_1$–$C_6$)alkylribose and/or 2'-[O-($C_1$–$C_6$)alkyl-O-($C_1$–$C_6$)alkyl]ribose, d) the complete or partial replacement of the natural nucleoside bases by 5-($C_2$–$C_6$)-alkynyluracil and/or 5-($C_2$–$C_6$)alkynylcytosine, e) the conjugation of the oligonucleotide to one or more molecules which independently of one another can be selected from the group comprising lipophilic molecules, e.g. ($C_{12}$–$C_{20}$)alkyl, lipids, e.g. 1,2-dihexadecyl-rac-glycerol, steroids, e.g. cholesterol and/or testosterone, vitamins, e.g. vitamin E, poly- or oligoethylene glycol, ($C_{12}$–$C_{18}$)-alkyl phosphate diesters and —O—$CH_2$—CH(OH)—O—($C_{12}$–$C_{18}$)-alkyl and f) one or more 3'—3' inversions at the 3' end of the oligonucleotide, in another preferred embodiment of the invention, the oligonucleotide has one or more chemical modifications which independently of one another can be selected from the group comprising:

a) the complete or partial replacement of the phosphoric acid diester bridges (phosphodiester bridges) by phosphorothioate bridges, b) the complete or partial replacement of the β-D-2'-deoxyribose units by 2'-F-2'-deoxyribose, 2'-O-($C_1$–$C_6$)alkylribose and/or 2'[O-($C_1$–$C_6$)alkyl-O-($C_1$–$C_6$)alkyl]ribose.

c) conjugation to lipophilic molecules, e.g. ($C_{12}$–$C_{20}$)-alkyl, to lipids, e.g. 1,2-dihexadecyl-rac-glycerol, to ($C_{12}$–$C_{18}$)alkyl phosphate diesters and/or to —O—$CH_2$—CH(OH)—O—($C_{12}$–$C_{18}$)-alkyl.

Processes for the preparation of an oligonucleotide conjugate are known to the person skilled in the art and are described, for example, in Uhlmann, E. & Peyman, A., Chem. Rev. 90 (1990) 543 and/or M. Manoharan in "Antisense Research and Applications", Crooke and Lebleu, Eds., CRC Press, Boca Raton, 1993, Chapter 17, p. 303ff. and/or EP-A 0 552 766.

In a particular embodiment of the invention, an oligonucleotide is made available which can have one or more modifications and which has one of the sequences SEQ ID NO. 2–SEQ ID NO. 20 or which corresponds to one of the sequences SEQ ID NO. 2 to SEQ ID NO. 20 or which corresponds to the appropriate sequence sections of a tenascin-coding sequence and can bind to this section of the tenascin-coding sequence.

In a particular embodiment of the invention, oligonucleotide is made available in whose sequence each nucleotide (base and/or sugar and/or internucleoside bridge) is modified. In a particular embodiment of the invention, for example, the oligonucleotide is completely synthesized from phosphorothioates (universally modified phosphorothioate, all internucleoside bridges modified). In a further specific embodiment of the invention, an oligonucleotide is made available which corresponds to one of the sequences SEQ ID NO. 2–SEQ ID NO. 20, but where the phosphodiester bridges between the individual nucleosides (i.e. the internucleoside bridges between the individual nucleosides) are completely replaced by phosphorothioate bridges (i.e., phosphorothioate groups between the nucleosides).

In a further particular embodiment of the invention, an oligonucleotide is made available by only replacing some of the phosphodiester bridges by phosphorothioate bridges. In particular, the invention comprises oligonucleotides which are only minimally (or partially) modified. The principle of the minimally modified oligonucleotides is described in A. Peyman, E. Uhlmann, Biol. Chem. Hoppe-Seyler, 377 (1996) 67–701 In this case, 1–5, preferably 1–3 terminal nucleotide units (preferably the corresponding internucleoside bridges) at the 5' and/or at the 3' end and, if appropriate, additionally selected internal pyrimidine positions or preferably the corresponding internucleoside bridges which are located at the 3' and/or 5' end of the corresponding pyrimidine nucleoside, are modified or replaced, internucleoside bridges preferably being replaced by phosphorothioate bridges. Oligonucleotides minimally modified in this way have particularly advantageous properties, for example they exhibit particular nuclease stability on minimal modification.

A particular embodiment of the invention relates to an oligonucleotide in which selected internucleoside bridges are replaced by modified internucleoside bridges, preferably by phosphorothioate bridges.

The invention relates to an oligonucleotide in which either
a) only certain phosphodiester internucleoside bridges or
b) all phosphodiester internucleoside bridges are modified.

The invention furthermore relates to an oligonucleotide in which 1–5 terminal internucleoside bridges are modified at the 5' and/or at the 3' end of the oligonucleotide. The invention also relates to an oligonucleotide in which the internucleoside bridges located at the 3' and/or 5' end of nonterminal nucleosides which contain a pyrimidine base (internal pyrimidine nucleosides) are modified.

Specific embodiments of the invention comprise a minimally modified oligonucleotide which has one of the sequences selected from the group consisting of the sequences SEQ ID NO. 21 to SEQ ID NO. 39, where
SEQ ID NO. 21: is 3'-GsGsTsTsTGGGTsGGAGGsTsGsG-5',
SEQ ID NO. 22: is 3'-GsGsAsGGTsGGTsACsCCsCCsGsG-5'
SEQ ID NO. 23: is 3'-GsGsTGGTsACsCsCCsCsGsG-5',
SEQ ID NO. 24: is 3'-GsGsAGGTsGGTsACsCsCsC-5',
SEQ ID NO. 25: is 3'-AsGsAAAGAAsCsGAAAGGsAsA-5',
SEQ ID NO. 26: is 3'-GsGsAGGTsGGTsAsCsC-5',
SEQ ID NO. 27: is 3'-GsGsAGCsGATsGGCsTsTsCsCsA-5',
SEQ ID NO. 28: is 3'-AsAsAGGAACsGGGAGsCsG-5',
SEQ ID NO. 29: is 3'-GsGsTCGGTsTsTGGGTsGsG-5',
SEQ ID NO. 30: is 3'-CsTsTACAGGTsCsCGTsTsGsA-5',
SEQ ID NO. 31: is 3'-GsGsCsCGsTGTsTCGCsTsGsT-5',
SEQ ID NO. 32: is 3'-TsCsACsCCsCTsCsTTsTsCsTsGsG-5',
SEQ ID NO. 33: is 3'-GsGsAsCACsCGACsACsGsG-5',
SEQ ID NO. 34: is 3'-AsAsCsGGGaGCGATsGsG-5',
SEQ ID NO. 35: is 3'-AsTsCsTCGGGGTsCsGsTsC-5',
SEQ ID NO. 36: is 3'-AsAsAGAACsGAAAGGsAsA-5',
SEQ ID NO. 37: is 3'-GsGsTGGTsACsCsCsC-5',
SEQ ID NO. 38: is 3'-CsCsCsGGTsACsTsGsA-5',
SEQ ID NO. 39: is 3'-CsCsAsCAGAAAGsAsAsC-5' and
  "s" indicating the position of a modified internucleoside bridge or dephospho bridge, "s" preferably indicating the position of a phosphorothioate bridge.

The sequences SEQ ID NO. 21 to SEQ ID NO. 39 correspond to the sequences SEQ ID NO. 2–SEQ ID NO. 20, i.e. they can bind to the same regions of a tenascin-coding sequence, where, however, in contrast to the SEQ ID NO. 2–20, some of the phosphodiester bridges are replaced by modified phosphodiester bridges or dephospho bridges, preferably by phosphorothioate bridges (in the sequence marked by an "s").

A further embodiment of the invention relates to chimeric oligonucleotides. A chimeric oligonucleotide is synthesized from at least two different sequence sections, for example from a DNA section and a modified section, e.g. a PNA section and/or a PHONA section. These different sections impart particular properties to the entire oligonucleotide.

A particular form of chimeric oligonucleotides is described, for example, in Matteucci and Wagner, Nature 384 SUPP (1996) 20–22. A chimeric oligonucleotide can contain, for example.
1. a so-called core sequence, which consists of approximately seven nucleotides and which can activate the RNase H, and
2. one or more flanking sequences which increase the affinity, specificity and/or nuclease stability of the oligonucleotide.

For example, the core sequence can have internucleoside bridges modified in certain positions, for example the core sequence can contain phosphorothioate and/or phosphodiester bridges. Suitable flanking sequences are, for example, sequences in which the sugar phosphate backbone (replacement of one or more sugar phosphate units) and/or β-D-2'-deoxyribose units are replaced. Suitable flanking sequences are, for example, PNAs and/or 2'-O-alkyl derivatives such as, for example, 2'-O-methyl and/or 2'-O-propyl and/or 2'-methoxyethoxy derivatives.

A particular embodiment of the invention relates to a chimeric oligonucleotide which has one of the sequences SEQ ID NO. 40–SEQ ID NO. 58, where
x independently of one another represents an unmodified or a modified phosphodiester internucleoside bridge or a dephospho bridge, preferably phosphorothioate and/or phosphorus diester
and
y independently of one another represents the replacement of a sugar phosphate until or a β-D-2'-deoxyribose unit, preferably 2'-O-methyl-, 2'-O-propyl- and/or 2'-methoxyethoxyribose or a PNA unit,
where
SEQ ID NO. 40: is 3'-GyGyTyTyTyGxGxGxTxGxGxAxGyGyTyGyG-5',
SEQ ID NO. 41: is 3'-GyGyAyGyGyTxGxGxTxAxCxCxCyCyCyGyG-5',
SEQ ID NO. 42: is 3'-GyGyTxGxGxTxAxCxCxCxCyCyGyG-5',
SEQ ID NO. 43: is 3'-GyGyAyGyGxTxGxGxTxAxCyCyCyC-5',
SEQ ID NO. 44: is 3'-AyGyAyAxAxGxAxAxCxGxAxAxAyGyGyAyA-5',
SEQ ID NO. 45: is 3'-GyGyAxGxGxTxGxGxTxAyCyC-5'.
SEQ ID NO. 46: is 3'-GyGyAxGxCxGxAxTxGyGyCyTyTyCyCyA-5',
SEQ ID NO. 47: is 3'-AyAyAyGxGxAxAxCxGxGyGyAyGyCyG-5', SEQ ID NO. 48: is 3'-GyGyTyCxGxGxTxTxTxGxGyGyTyGyG-5',
SEQ ID NO. 49: is 3'-CyTyTyAxCxAxGxGxTxCxCxGyTyTyGyA-5',
SEQ ID NO. 50: is 3'-GyGyCyCxGxTxGxTxTxCxGyCyTyGyT-5',
SEQ ID NO. 51: is 3'-TyCyAyCxCxCxCxTxCxTxTyTyCyTyGyG-5',
SEQ ID NO. 52: is 3'-GyGyAyCxAxCxCxGxAxCxAyCyGyG-5',
SEQ ID NO. 53: is 3'-AyAyCyGxGxGxAxGxCxGxAyTyGyG-5',
SEQ ID NO. 54: is 3'-AyTyCyTxCxGxGxGxGxTxCxGyTyC-5',
SEQ ID NO. 55: is 3'-AyAAyGxAxAxCxGxAxAxAxGyGyAyA-5',
SEQ ID NO. 56: is 3'-GyGyTxGxGxTxAxCxCyCyC-5',
SEQ ID NO. 57: is 3'-CyCxCxGxGxTxAxCyTyGyA-5',
SEQ ID NO. 58: is 3'-CyCyAxCxAxGxAxAxAxGyAyAyC-5'.

The sequences SEQ ID NO. 40–SEQ ID NO. 58 correspond to the abovementioned sequences SEQ ID NO. 2 to SEQ ID NO. 20, i.e. they bind to the corresponding sequence sections of a tenascin-coding sequence, where, however, the modifications mentioned are present.

The invention relates to processes for the preparation of the oligonucleotides. The oligonucleotides described can be prepared with the aid of various known, chemical processes, e.g. applying the standard phosphoramidite chemistry using iodine or TED (tetraethylthiuram disulfide) as oxidant. This process is described, for example, in Eckstein, F. (1991) "Oligonucleotides and Analogues, A practical Approach", IRL Press, Oxford. The oligonucleotides can also be prepared by processes which optionally contain one or more enzymatic steps.

The invention relates to the use of the oligonucleotides. The oligonucleotides can be used for hybridization or binding to tenascin-coding (single-stranded and/or double-stranded) nucleic acids, for example DNA relates to the use of the oligonucleotides for hybridization with or binding to nucleic acids which have the sequence SEQ ID NO. 1 according to Table 1 or with nucleic acids which have parts of this sequence (for example sequences which code for tenascin isoforms) or with nucleic acids whose sequence differs sightly from these sequences (which have, for example, one or more point mutations).

The invention furthermore relates to the use of the oligonucleotides for the modulation and for the complete or partial inhibition of the expression of tenascin or various tenascin isoforms or of mutants thereof, for example for the complete or partial inhibition of transcription and/or of translation.

The invention relates, for example, to the use of the oligonucleotides as antisense oligonucleotides. Moreover, the oligonucleotides can be used as aids in molecular biology.

The invention furthermore relates to the use of the oligonucleotides as pharmaceutical and/or diagnostic or the use of the oligonucleotides for the production of pharmaceuticals and/or diagnostics. In particular, the oligonucleotides can be employed in pharmaceuticals which are suitable for the prevention and/or treatment of diseases which accompany the expression of an overexpression of tenascin. Since the expression of tenascin is normally, i.e., for example, in the healthy person, limited spatially and temporally, a deviation from this normal spatial and temporal expression can be regarded as overexpression. Furthermore, the oligonucleotides can be employed in diagnostic processes. Such diagnostic processes can be employed, for example, for the diagnosis or early recognition of diseases which accompany abnormally expression (e.g., overexpression) of tenascin.

The invention also relates to a test kit which contains one or more oligonucleotides according to the invention and, if appropriate, further components. Such a test kit can be employed, for example, in diagnosis and as a precaution, for example against skin cancer disorders.

The invention further relates to the use of the oligonucleotides or of pharmaceuticals which contain these oligonucleotides for the treatment of diseases in which tenascin or an overexpression of tenascin is the cause or is involved.

The invention relates in particular to the use of the oligonucleotides or of pharmaceuticals which contain these oligonucleotides for the treatment and/or prevention of diseases in which a dysregulation or disorder of the immigration or of the presence or of the inclusion of melanocytes in epithelial cell layers, for example in the epithelial cell layer of the epidermis, of the choroid membrane of the eye or of the substantia nigra as the basis serves or is involved and of Addison's disease, diabetes mellitus, pernicious anemia and/or thyroid gland dysfunctions.

The invention relates in particular to the use of the oligonucleotides or of pharmaceuticals which contain these oligonucleotides for the treatment and/or prevention of vitiligo and other depigmentation diseases or depigmentation disorders (e.g. of the skin, hair, eyes) for example albinism and/or for the treatment of psoriasis and/or for the treatment of cancer, e.g. for the inhibition of tumor growth and tumor metastasis, for example in melanomas and/or for the treatment of inflammations, in particular as antiinflammatories and/or for the treatment and/or prophylaxis of cardiovascular disorders, for example of restenosis.

In particular, the invention relates to the use of the oligonucleotides for the treatment of vitiligo or for the production of pharmaceuticals which can be used for the treatment of vitiligo. The invention moreover relates quite generally (i.e. also oligonucleotides having a length of greater than or equal to 18 nucleotides) to the use of oligonucleotides for the treatment of vitiligo or the production of pharmaceuticals which can be used for the treatment of vitiligo.

The invention furthermore relates to the use for the treatment of vitiligo in combination with known therapeutic processes, for example in combination a) with photochemotherapy (PUVA), e.g. using methoxypsoralen, phenylalaine and/or khellin and/or b) with the transplantation of cultured melanocytes (epidermal grafting) and/or c) with a steroid treatment and/or d) with a treatment with placenta extracts and/or e) with a treatment with pseudocatalase.

The invention furthermore relates to processes for the production of pharmaceuticals (pharmaceutical preparations). For the production of pharmaceuticals, one or more different oligonucleotides or their physiologically tolerable salts are mixed, it optionally being possible to add further pharmaceutical vehicles and/or additives.

The invention furthermore relates to pharmaceutical preparations (pharmaceuticals), which contain one or more different oligonucleotides and/or their physiologically tolerable salts, and, if appropriate, pharmaceutical vehicles and/or additives.

The oligonucleotide(s) and/or its/their physiologically tolerable salts can be administered to animals, preferably to mammals, in particular to humans as pharmaceuticals on its/their own, in mixtures with one another or in the form of pharmaceutical preparations. The pharmaceuticals can make possible topical, percutaneous, parenteral and/or enteral administration. The administration form preferred in each case depends on the specific conditions in each case. For the treatment of vitiligo, for example, a topical application, e.g., in the form of ointments, lotions or tinctures, emulsions or suspensions, is preferred. Likewise, the frequency of the administration depends on the individual conditions. For the treatment of vitiligo, for example, a topical composition can be applied to the depigmented skin site one to two times during the day.

As active constituent, pharmaceuticals or pharmaceutical preparations can contain an efficacious dose of at least one oligonucleotide and/or a mixture of a number of oligonucleotides and, if appropriate, additional, pharmaceutically innocuous vehicles and/or additives. Pharmaceutical preparations can contain approximately 0.1% (percent by weight) or less up to approximately 90% (percent by weight) or more of the therapeutically active oligonucleotide or the pharmaceutically active oligonucleotide.

The pharmaceutically efficacious dose of the respective oligonucleotide or of an oligonucleotide which is a constituent of a mixture of various oligonucleotides can vary within wide limits and is to be adapted to the individual conditions in each individual case.

The production of the pharmaceutical preparations can be carried out in a manner known per se, e.g. described in Remingtons Pharmaceutical Sciences (1985), Mack Publ. Co., Easton, Pa., it optionally being possible to use pharmaceutically inert inorganic and/or organic vehicles. For the production of pills, tablets, coated tablets and/or hard gelatin capsules, it is possible to use, for example, lactose, cornstarch and/or derivatives thereof, talc, stearic acid and/or its salts. Vehicles which can be used for soft gelatin capsules and/or suppositories are, for example, fats, waxes, semisolid and/or liquid polyols, natural and/or hardened oils. Vehicles which can be used for the production of solutions and/or syrups are, for example, water, sucrose, invert sugar, glucose and/or polyols. Vehicles which can be used for the production of injection solutions are, for example, water, alcohols, glycerol, polyols and/or vegetable oils. Vehicles which can be used for microcapsules, implants and/or rods are, for example, copolymers, e.g., of glycolic acid and lactic acid. Moreover, liposome formulations which are known to the person skilled in the art (N. Weiner, Drug Develop Ind Pharm 15 (1989) 1523; "Liposome Dermatics, Springer Verlag 1992), for example HVJ liposomes (Hayashi, Gene Therapy 3 (1996) 878) are suitable. Dermal administration can be carried out, for example, also with the aid of ionophoretic methods and/or with the aid of electroporation. Moreover, lipofectins and/or other (nucleic acid or DNA) carrier systems, for example those which are used in gene therapy, can be used. In particular, suitable systems are those with whose aid oligonucleotides can be introduced into eukaryotic cells or the nuclei of eukaryotic cells with great efficiency.

In addition to the active compounds and vehicles, a pharmaceutical preparation can additionally contain additives, such as, for example, fillers, extenders, disintegrants, binding agents, lubricants, wetting agents, stabilizers, emulsifiers, preservatives, sweeteners, colorants, flavorings or aromatizers, thickening agents, diluents, buffer substances, furthermore solvents and/or solubilizers and/or agents for achieving a depot effect, and salts for changing the osmotic pressure, coating agents and/or antioxidants. They can also contain two or more different oligonucleotides and/or their physiologically tolerable salts and furthermore, in addition to at least one oligonucleotide, one or more other therapeutically active substances.

EXAMPLES

Example 1

Oligonucleotide synthesis

The oligonucleotide was synthesized on an automatic DNA synthesizer (Applied Biosystems Model 380B or 394) using the standard phosphoramidite chemistry and oxidation with iodine (F. Eckstein, Ed. "Oligonucleotides and Analogs, A practical Approach", IRL Press, Oxford, 1991). For the introduction of phosphorothioate bridges in mixed phosphorothioates and phosphodiester oligonucleotide, oxidation was carried out with TETD (tetraethylthiuram disulfide) instead of iodine (Applied Biosystems User Bulletin 65). After removal of solid carrier (CPG or Tentagel) and removal of the protective groups with conc. $NH_3$ at 55° C. (18 h), the oligonucleotide was first purified by butanol precipitation (Sawadogo, Van Dyke, Nucl. Acids. Res. 19 (1991) 674). The sodium salt was then obtained by precipitation from a 0.5 M NaCl solution using 2.5 parts by volume of ethanol.

The oligonucleotide was analyzed with the aid of a) analytical gel electrophoresis (gel: 20% acrylamide, 8M urea; running buffer: 454M tris borate buffer, pH 7.0) and/or b) HPLC analysis (column material: Waters GenPak FAX; gradient: $CH_3CN$ (400 ml), $H_2O$ (1.6 l), $NaH_2PO_4$ (3.1 g), NaCl (11.7 g) pH 6.8 (0.1 M in NaCl) after $CH_3CN$ (400 ml), $H_2O$ (1.6 l), $NaH_2PO_4$ (3.1 g), NaCl (175.3 g), pH 6.8 (1.5 M in NaCl)) and/or c) capillary gel electrophoresis (Beckmann capillary eCAP™, U100P gel column, 65 cm length, 100 mm I.D. window 15 cm from one end; buffer: 140 µM tris, 360 mM boric acid, 7M urea) and/or d) electrospray mass spectroscopy.

The analysis of the oligonucleotide showed that this was in each case present in a purity of greater than 90%. The methods for the analysis of oligonucleotides are described, for example, in Schweiber and Engler "Analysis of oligonucleotides" (in "Antisense—from technology to therapy", a laboratory manual and textbook, Schlingensiepen et al. eds., Biol. Science, Vol. 6 (1997) p. 78–103).

Synthesized oligonucleotide:

ODN1 (Sequence SEQ ID NO. 24): 3'-GsGsAGGTsGGTsACsCsCsC-5'

Example 2

Production of a pharmaceutical preparation 50 mg of ODN 1 from Example 1 can be closely mixed with 1 g of Dermatop® (Hoechst Aktiengesellschaft, Frankfurt am Main, Germany) base cream and the mixture stored at temperatures of <10° C.

Example 3

The cream from Example 2 can then be applied twice daily (in the morning and afternoon or evening) to a depigmented skin site of a vitiligo patient.

What is claimed is:

1. An oligonucleotide or physiologically tolerable salt thereof, comprising a sequence selected from SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, and SEQ ID NO. 11, wherein the oligonucleotide has a maximum length of 17 nucleotide units.

2. An oligonucleotide or physiologically tolerable salt thereof, comprising a sequence selected from SEQ ID NO: 2, SEQ ID NO: 3, SEQ ID NO: 4, SEQ ID NO: 5, SEQ ID NO: 6, SEQ ID NO: 7, SEQ ID NO: 7, SEQ ID NO: 8, SEQ ID NO: 9, SEQ ID NO: 10, and SEQ ID NO: 11, wherein the oligonucleotide has a maximum length of 17 nucleotide units, and wherein the oligonucleotide has one or more modifications.

3. The oligonucleotide according to claim 2, wherein the modifications are independently selected from the group consisting of:

a) the replacement of a phosphoric acid diester internucleoside bridge by a modified phospho bridge, b) the replacement of a phosphoric acid diester internucleoside bridge by a "dephospho" bridge, c) the replacement of a sugar phosphate unit by another unit, d) the replacement of a β-D-2'-deoxyribose unit by a modified sugar unit, e) the modification or the replacement of a natural nucleoside base by a modified nucleoside base, f) the conjugation of the oligonucleotide to a molecule which adapts the properties of the oligonucleotide to a specific requirement, g) the conjugation of the oligonucleotide to a 2'5'-bonded oligoadenylate or a derivative thereof, optionally conjugated via a linker, and h) the introduction of a 3'-3' or 5'-5'inversion at the 3' or 5' end of the oligonucleotide.

4. The oligonucleotide according to claim 3, wherein the oligonucleotide contains one or more modifications independently selected from the group consisting of:

a) the replacement of a phosphoric acid diester internucleoside bridge by a modified phospho bridge, where a modified phospho bridge is a phosphorothioate, phosphorodithioate, NR$^1$R$^1$-phosphoramidate, boranophosphate, phosphate-$(C_1-C_{21})$-O-alkyl ester, phosphate-$[(C_6-C_{12})$aryl-$(C_1-C_{21})$-O-alkyl] ester, $(C_1-C_8)$alkylphosphonate, or $(C_6-C_{12})$ arylphosphonate bridge, where $R^1$ and $R^{1'}$ are independently selected from the group comprising hydrogen, $(C_1-C_{18})$-alkyl, $(C_6-C_{20})$-aryl, $(C_6-C_{14})$-aryl-$(C_1-C_8)$-alkyl, or $R^1$ and $R^{1'}$, together with the nitrogen atom carrying them, form a 5- to 6-membered heterocyclic ring which can additionally contain a further heteroatom from the group consisting of O, S, and N;

b) the replacement of a phosphoric acid diester internucleoside bridge by a "dephospho" bridge, where a "dephospho" bridge is a formacetal, 3'-thioformacetal, methylhydroxylamine, oxime, methylenedimethylhydrazo, dimethylenesulfone, or silyl bridge, c) the complete or partial replacement of the sugar phosphate backbone (replacement of sugar phosphate units) by other units, where another units is suitable for synthesizing a "morpholine derivative" oligomer, a polyamide nucleic acid ("PNA"), or a phosphomonoacid ester nucleic acid, d) the replacement of a β-D-2'-deoxyribose unit by a modified sugar unit, where a modified sugar unit is an α-D-2'-deoxyribose, L-2'-deoxyribose, 2'-F-2'-deoxyribose, 2'-O-$(C_1-C_6)$ alkylribose, 2'-O-$(C_2-C_6)$alkenylribose, 2'-[O-$(C_1-C_6)$ alkyl-O-$(C_1-C_6)$alkyl]ribose, 2'-$NH_2$-2'-deoxyribose, β-D-xylofuranose, α-arabinofuranose, 2,4-dideoxy-β-D-erythro-hexopyranose, a carbocyclic sugar analog, an open-chain sugar analog, or a bicyclo sugar analog, e) the replacement of a natural nucleoside base by a modified nucleoside base, where a modified nucleoside base is 5-(hydroxymethyl) uracil, 5 aminouracil, pseudouracil, dihydrouracil, 5-$(C_1-C_6$-alkyluracil, 5-$(C_2-C_6)$-alkenyluracil, 5-$(C_2-C_6)$-alkynyluracil, 5-$(C_1-C_5)$-alkylcytosine, 5-$(C_2-C_6)$-alkenylcytosine, 5-$(C_2-C_6)$-alkynylcytosine, 5-fluorouracil, 5-fluorocytosine, 5-chlorouracil, 5-chlorocytosine, 5-bromouracil, 5-bromocytosine, a 7-deaza-7-substituted purine, or a 7-deaza-8-substituted purine, f) conjugation to a molecule, where the molecule is a polylysine, intercalator, fluorescent molecule, crosslinker, lipophilic molecule, lipid, steroid, vitamin, polyethylene glycol, oligoethylene glycol, $(C_{12}-C_{18})$-alkyl phosphate diester, or —O—$CH_2$—CH(OH)—O—$(C_{12}-C_{18})$-alkyl group, g) conjugation to a 2'5'-linked oligoadenylate or a derivative thereof where a 2'5'-linked oligoadenylate or a derivative thereof is a 2'5'-linked triadenylate, 2'5'-linked tetraadenylate, 2'5'-linked pentaadenylate, or cordycepin (2'5'-linked 3'-deoxyadenylate), where the conjugation optionally takes place via a linker and where the 5'-end of the 2'5'-linked oligoadenylate optionally contains a phosphate, diphosphate, or triphosphate group, and h) the introduction of a 3'—3' or 5'—5' inversion at the 3'- or 5'-end of the oligonucleotide.

5. The oligonucleotide according to claim 3, wherein 1–5 terminal internucleoside bridges are modified at the 5- or 3'-end of the oligonucleotide.

6. The oligonucleotide according to claim 3, wherein the internucleoside bridges located at the 3'- or 5'-end of nonterminal nucleosides which contain a pyrimidine base are modified.

7. The oligonucleotide according to claim 3, comprising a sequence selected from SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29 and SEQ ID NO. 30, where "s" in the recited SEQ ID NOs. indicates the position of a modified internucleoside bridge.

8. The oligonucleotide according to claim 3, comprising a sequence selected from SEQ ID N. 40, SEQ ID NO. 41, SEQ ID NO. 42, SEQ ID NO. 43, SEQ ID NO. 44, SEQ ID NO. 45, SEQ ID NO. 46, SEQ ID NO. 47, SEQ ID NO. 48 and SEQ ID NO. 49, where "x" in the recited SEQ ID NOs., independently of one another, represents a phosphodiester internucleoside bridge or a modified internucleoside bridge, and "y" in the recited SEQ ID NOs., independently of one another, represents the replacement of a sugar phosphate unit or of a β-D-2'-deoxyribose unit, the modified β-D-2'-deoxyribose unit being located at the 3'-end of "y".

9. The oligonucleotide according to claim 8, where "y" represents 2' O-methyl-, 2'-O-propyl- or 2'-methoxyethoxyribose, or a PNA unit.

10. A process for the preparation of an oligonucleotide according to claim 7, said process comprising synthesizing the oligonucleotide on a solid phase.

11. A diagnostic comprising one or more oligonucleotides according to claim 7.

12. A test kit comprising one or more oligonucleotides according to claim 7.

13. The oligonucleotide of claim 7, wherein the oligonucleotide consists of SEQ ID NO: 21.

14. The oligonucleotide of claim 7, wherein the oligonucleotide consists of SEQ ID NO: 22.

15. The oligonucleotide of claim 7, wherein the oligonucleotide consists of SEQ ID NO: 23.

16. The oligonucleotide of claim 7, wherein the oligonucleotide consists of SEQ ID NO:24.

17. The oligonucleotide of claim 7, wherein the oligonucleotide consists of SEQ ID NO:25.

18. The oligonucleotide of claim 7, wherein the oligonucleotide consists of SEQ ID NO:26.

19. The oligonucleotide of claim 7, wherein the oligonucleotide consists of SEQ ID NO:27.

20. The oligonucleotide of claim 7, wherein the oligonucleotide consists of SEQ ID NO:28.

21. The oligonucleotide of claim 7, wherein the oligonucleotide consists of SEQ ID NO:29.

22. The oligonucleotide of claim 7, wherein the oligonucleotide consists of SEQ ID NO:30.

23. An in vitro method for inhibiting expression of tension by a cell, said method comprising exposing said cell to an oligonucleotide comprising a sequence selected from SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29; and SEQ ID NO:30, wherein the oligonucleotide has a maximum length of 17 nucleotide units.

* * * * *

SEQUENCE LISTING

<160> NUMBER OF SEQ ID NOS: 58

<210> SEQ ID NO 1
<211> LENGTH: 7346
<212> TYPE: DNA
<213> ORGANISM: Homo sapiens

<400> SEQUENCE: 1

| | | | | | |
|---|---|---|---|---|---|
| gaattcgcta | gagccctaga | gccccagcag | cacccagcca | aacccacctc | caccatgggg | 60 |
| gccatgactc | agctgttggc | aggtgtcttt | cttgctttcc | ttgccctcgc | taccgaaggt | 120 |
| ggggtcctca | agaaagtcat | ccggcacaag | cgacagagtg | gggtgaacgc | caccctgcca | 180 |
| gaagagaacc | agccagtggt | gtttaaccac | gtttacaaca | tcaagctgcc | agtgggatcc | 240 |
| cagtgttcgg | tggatctgga | gtcagccagt | ggggagaaag | acctggcacc | gccttcagag | 300 |
| cccagcgaaa | gctttcagga | gcacacagta | gatgggaaaa | accagattgt | cttcacacat | 360 |
| cgcatcaaca | tcccccgccg | ggcctgtggc | tgtgccgcag | ccctgatgt | taaggagctg | 420 |
| ctgagcagac | tggaggagct | ggagaacctg | gtgtcttccc | tgagggagca | atgtactgca | 480 |
| ggagcaggct | gctgtctcca | gcctgccaca | ggccgcttgg | acaccaggcc | cttctgtagc | 540 |
| ggtcggggca | acttcagcac | tgaaggatgt | ggctgtgtct | gcgaacctgg | ctggaaaggc | 600 |
| cccaactgct | ctgagcccga | atgtccaggc | aactgtcacc | ttcgaggccg | tgcattgat | 660 |
| gggcagtgca | tctgtgacga | cggcttcacg | ggcgaggact | gcagccagct | ggcttgcccc | 720 |
| agcgactgca | atgaccaggg | caagtgcgtg | aatggagtct | gcatctgttt | cgaaggctac | 780 |
| gcggctgact | gcagccgtga | aatctgccca | gtgccctgca | gtgaggagca | cggcacatgt | 840 |
| gtagatggct | tgtgtgtgtg | ccacgatggc | tttcaggcg | atgactgcaa | caagcctctg | 900 |
| tgtctcaaca | attgctacaa | ccgtggacga | tgcgtggaga | tgagtgcgt | gtgtgatgag | 960 |
| ggtttcacgg | gcgaagactg | cagtgagctc | atctgcccca | atgactgctt | cgaccggggc | 1020 |
| cgctgcatca | atggcacctg | ctactgcgaa | gaaggcttca | caggtgaaga | ctgcgggaaa | 1080 |
| cccacctgcc | cacatgcctg | ccacacccag | ggccgtgtg | aggagggca | gtgtgtatgt | 1140 |
| gatgagggct | tgccggtgt | ggactgcagc | gagaagaggt | gtcctgctga | ctgtcacaat | 1200 |
| cgtggccgct | gtgtagacgg | gcggtgtgag | tgtgatgatg | gtttcactgg | agctgactgt | 1260 |
| ggggagctca | agtgtcccaa | tggctgcagt | ggccatggcc | gctgtgtcaa | tgggcagtgt | 1320 |
| gtgtgtgatg | agggctatac | tggggaggac | tgcagccagc | tacggtgccc | caatgactgt | 1380 |
| cacagtcggg | gccgctgtgt | cgagggcaaa | tgtgtatgtg | agcaaggctt | caagggctat | 1440 |
| gactgcagtg | acatgagctg | ccctaatgac | tgtcaccagc | acggccgctg | tgtgaatggc | 1500 |
| atgtgtgttt | gtgatgacgg | ctacacaggg | gaagactgcc | gggatcgcca | atgccccagg | 1560 |
| gactgcagca | cagggggcct | ctgtgtggac | ggacagtgcg | tctgtgagga | cggcttcacc | 1620 |
| ggccctgact | gtgcagaact | ctcctgtcca | aatgactgcc | atggccaggg | tcgctgtgtg | 1680 |
| aatgggcagt | gcgtgtgcca | tgaaggattt | atgggcaaag | actgcaagga | gcaaagatgt | 1740 |
| cccagtgact | gtcatggcca | gggccgctgc | gtggacggcc | agtgcatctg | ccacgagggc | 1800 |
| ttcacaggcc | tggactgtgg | ccagcactcc | tgccccagtg | actgcaacaa | cttaggacaa | 1860 |
| tgcgtctcgg | gccgctgcat | ctgcaacgag | ggctacagcg | agaagactg | ctcagaggtg | 1920 |
| tctcctccca | aagacctcgt | tgtgacagaa | gtgacggaag | agacggtcaa | cctggcctgg | 1980 |
| gacaatgaga | tgcgggtcac | agagtacctt | gtcgtgtaca | cgcccacccca | cgagggtggt | 2040 |

```
ctggaaatgc agttccgtgt gcctggggac cagacgtcca ccatcatccg ggagctggag    2100
cctggtgtgg agtactttat ccgtgtattt gccatcctgg agaacaagaa gagcattcct    2160
gtcagcgcca gggtggccac gtacttacct gcacctgaag gcctgaaatt caagtccatc    2220
aaggagacat ctgtggaagt ggagtgggat cctctagaca ttgcttttga aacctgggag    2280
atcatcttcc ggaatatgaa taaagaagat gagggagaga tcaccaaaag cctgaggagg    2340
ccagagacct cttaccggca aactggtcta gctcctgggc aagagtatga gatatctctg    2400
cacatagtga aaacaatac ccggggccct ggcctgaaga gggtgaccac cacacgcttg    2460
gatgccccca gccagatcga ggtgaaagat gtcacagaca ccactgcctt gatcacctgg    2520
ttcaagcccc tggctgagat cgatggcatt gagctgacct acggcatcaa agacgtgcca    2580
ggagaccgta ccaccatcga tctcacagag gacgagaacc agtactccat cgggaacctg    2640
aagcctgaca ctgagtacga ggtgtccctc atctcccgca gaggtgacat gtcaagcaac    2700
ccagccaaag agaccttcac aacaggcctc gatgctccca ggaatcttcg acgtgtttcc    2760
cagacagata acagcatcac cctggaatgg aggaatggca aggcagctat tgacagttac    2820
agaattaagt atgcccccat ctctggaggg gaccacgctg aggttgatgt tccaaagagc    2880
caacaagcca caaccaaaac cacactcaca ggtctgaggc cgggaactga atatgggatt    2940
ggagtttctg ctgtgaagga agacaaggag agcaatccag cgaccatcaa cgcagccaca    3000
gagttggaca cgcccaagga ccttcaggtt tctgaaactg cagagaccag cctgacccctg   3060 ctctggaaga caccgttggc caaatttgac cgctaccgcc tcaattacag tctccccaca    3120
ggccagtggg tgggagtgca gcttccaaga acaccactt cctatgtcct gagaggcctg    3180
gaaccaggac aggagtacaa tgtcctcctg acagccgaga aggcagacaa caagagcaag    3240
cccgcacgtg tgaaggcatc cactgaacaa gcccctgagc tggaaaacct caccgtgact    3300
gaggttggct gggatggcct cagactcaac tggaccgcgg ctgaccaggc ctatgagcac    3360
tttatcattc aggtgcagga ggccaacaag gtggaggcag ctcggaacct caccgtgcct    3420
ggcagccttc gggctgtgga cataccgggc ctcaaggctc ctacgcctta cagtctcc    3480 atctatgggg tgatccaggg ctatagaaca ccagtgctct ctgctgaggc ctccacaggg    3540
gaaactccca atttgggaga ggtcgtggtg gccgaggtgg gctgggatgc cctcaaactc    3600
aactggactg ctccagaagg ggcctatgag tactttttca ttcaggtgca ggaggctgac    3660
acagtagagg cagcccagaa cctcaccgtc ccaggaggac tgaggtccac agacctgcct    3720
gggctcaaag cagccactca ttataccatc accatccgcg gggtcactca ggacttcagc    3780
acaacccctc tctctgttga agtcttgaca gaggaggttc cagatatggg aaacctcaca    3840
gtgaccgagg ttagctggga tgctctcaga ctgaactgga ccacgccaga tggaacctat    3900 gaccagtttta ctattcaggt ccaggaggct gaccaggtgg aagaggctca caatctcacg    3960
gttcctggca gcctgcgttc catggaaatc ccaggcctca gggctggcac tccttacaca    4020
gtcaccctgc acggcgaggt cagggccac agcactcgac cccttgctgt agaggtcgtc    4080
cagtgggacg tgccgctcca gtccccggtg tcgtgagctg gggaacgaca tctccagcag    4140
acagaggatc tcccacagct gggagattta gccgtgtctg aggttggctg ggatggcctc    4200
agactcaact ggaccgcagc tgacaatgcc tatgagcact ttgtcattca ggtgcaggag    4260
gtcaacaaag tggaggcagc ccagaacctc acgttgcctg gcagcctcag ggctgtggac    4320
atcccgggcc tcgaggctgc cacgccttat agagtctcca tctatggggt gatccggggc    4380
```

```
tatagaacac cagtactctc tgctgaggcc tccacagcca agaaacctga aattggaaac    4440
ttaaatgttt ctgacataac tcccgagagc ttcaatctct cctggatggc taccgatggg    4500
atcttcgaga cctttaccat tgaaattatt gattccaata ggttgctgga gactgtggaa    4560
tataatatct ctggtgctga acgaactgcc catatctcag ggctaccccc tagtactgat    4620
tttattgtct acctctctgg acttgctccc agcatccgga ccaaaaccat cagtgccaca    4680
gccacgacag aggccctgcc ccttctggaa aacctaacca tttccgacat taatccctac    4740
gggttcacag tttcctggat ggcatcggag aatgcctttg acagctttct agtaacggtg    4800
gtggattctg ggaagctgct ggaccccag gaattcacac tttcaggaac ccagaggaag    4860
ctggagctta gaggcctcat aactggcatt ggctatgagg ttatggtctc tggcttcacc    4920
caagggcatc aaaccaagcc cttgagggct gagattgtta cagaagccga accgaagtt    4980 gacaaccttc tggtttcaga tgccaccca gacggtttcc gtctgtcctg acagctgat    5040 gaagggtct tcgacaattt tgttctcaaa atcagagata ccaaaaagca gtctgagcca    5100
ctggaaataa ccctacttgc ccccgaacgt accagggaca taacaggtct cagagaggct    5160
actgaatacg aaattgaact ctatggaata agcaaaggaa ggcgatccca gacagtcagt    5220
gctatagcaa caacagccat gggctcccca aaggaagtca ttttctcaga catcactgaa    5280
aattcggcta ctgtcagctg gagggcaccc acggcccaag tggagagctt ccggattacc    5340
tatgtgccca ttacaggagg tacaccctcc atggtaactg tggacggaac caagactcag    5400
accaggctgg tgaaactcat acctggcgtg gagtaccttg tcagcatcat cgccatgaag    5460
ggctttgagg aaagtgaacc tgtctcaggg tcattcacca cagctctgga tggcccatct    5520
ggcctggtga cagccaacat cactgactca gaagccttgg ccaggtggca gccagccatt    5580
gccactgtgg acagttatgt catctcctac acaggcgaga agtgccaga aattacacgc    5640 acggtgtccg ggaacacagt ggagtatgct ctgaccgacc tcgagcctgc cacggaatac    5700
acactgagaa tctttgcaga gaagggccc cagaagagct caaccatcac tgccaagttc    5760
acaacagacc tcgattctcc aagagacttg actgctactg aggttcagtc ggaaactgcc    5820
ctccttacct ggcgaccccc ccgggcatca gtcaccggtt acctgctggt ctatgaatca    5880
gtggatggca cagtcaagga agtcattgtg ggtccagata ccacctccta cagcctggca    5940
gacctgagcc catccaccca ctacacagcc aagatccagg cactcaatgg gcccctgagg    6000
agcaatatga tccagaccat cttcaccaca attggactcc tgtacccctt ccccaaggac    6060
tgctcccaag caatgctgaa tggagacacg acctctggcc tctacaccat ttatctgaat    6120
ggtgataagg ctcaggcgct ggaagtcttc tgtgacatga cctctgatgg gggtggatgg    6180
attgtgttcc tgagacgcaa aaacggacgc gagaacttct accaaaactg gaaggcatat    6240
gctgctggat ttgggaccg cagagaagaa ttctggcttg gctggacaa cctgaacaaa    6300 atcacagccc aggggcagta cgagctccgg gtggacctgc gggaccatgg ggagacagcc    6360
tttgctgtct atgacaagtt cagcgtggga gatgccaaga ctcgctacaa gctgaaggtg    6420 gagggtaca gtgggacagc aggtgactcc atggcctacc acaatggcag atccttctcc    6480
acctttgaca aggacacaga ttcagccatc accaactgtg ctctgtctac aagggcttc    6540 tggtacagga actgtcaccg tgtcaacctg atggggagat atgggacaa taaccacagt    6600 cagggcgtta actggttcca ctggaagggc cacgaacact caatccagtt tgctgagatg    6660
aagctgagac caagcaactt cagaaatctt gaaggcaggc gcaaacgggc ataaattgga    6720
gggaccactg ggtgagagag gaataaggcg gcccagagcg aggaaaggat tttaccaaag    6780
```

```
catcaataca accagcccaa ccatcggtcc acacctgggc atttggtgag aatcaaagct    6840
gaccatggat ccctggggcc aacggcaaca gcatgggcct cacctcctct gtgatttctt    6900
tctttgcacc aaagacatca gtctccaaca tgtttctgtt ttgttgtttg attcagcaaa    6960
aatctcccag tgacaacatc gcaatagttt tttacttctc ttaggtggct ctgggatggg    7020 agagggtag gatgtacagg ggtagtttgt tttagaacca gccgtatttt acatgaagct    7080
gtataattaa ttgtcattat ttttgttagc aaagattaaa tgtgtcattg gaagccatcc    7140 cttttttttac atttcataca acagaaacca gaaaagcaat actgtttcca ttttaaggat    7200
atgattaata ttattaatat aataatgatg atgatgatga tgaaaactaa ggattttca    7260 agagatcttt ctttccaaaa catttctgga cagtacctga ttgtatttt tttttaaata    7320 aaagcacaag tacttttgaa aaaaaa                                        7346
```

```
<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggtggaggtg ggtttgg                                                    17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcccccatg gtggagg                                                    17

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcccccatg gtgg                                                       14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccccatggtg gagg                                                       14

<210> SEQ ID NO 6
<211> LENGTH: 17
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 6
aaggaaagca agaaaga                                                    17

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccatggtgga gg                                                         12

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
accttcggta gcgagg                                                     16

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcgagggcaa ggaaa                                                      15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggtgggtttg gctgg                                                      15

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agttgcctgg acattc                                                     16

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
tgtcgcttgt gccgg                                             15

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggtctttctc cccact                                            16

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggcacagcca cagg                                              14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggtagcgagg gcaa                                              14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctgctggggc tcta                                              14

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaggaaagca agaaa                                             15

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 18
ccccatggtg g                                                        11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agtcatggcc c                                                        11

<210> SEQ ID NO 20
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
caagaaagac acc                                                      13

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggtggaggtg ggtttgg                                                  17

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcccccatg gtggagg                                                  17

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggcccccatg gtgg                                                     14

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 24
ccccatggtg gagg                                                          14

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaggaaagca agaaaga                                                       17

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ccatggtgga gg                                                            12

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
accttcggta gcgagg                                                        16

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcgagggcaa ggaaa                                                         15

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggtgggtttg gctgg                                                         15

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
```
agttgcctgg acattc                                                              16

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgtcgcttgt gccgg                                                               15

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggtctttctc cccact                                                              16

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggcacagcca cagg                                                                14

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggtagcgagg gcaa                                                                14

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ctgctggggc tcta                                                                14

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

|  |  |
|---|---|
| aaggaaagca agaaa | 15 |

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37

|  |  |
|---|---|
| ccccatggtg g | 11 |

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38

|  |  |
|---|---|
| agtcatggcc c | 11 |

<210> SEQ ID NO 39
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39

|  |  |
|---|---|
| caagaaagac acc | 13 |

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40

|  |  |
|---|---|
| ggtggaggtg ggtttgg | 17 |

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41

|  |  |
|---|---|
| ggcccccatg gtggagg | 17 |

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42

|  |  |
|---|---|
| ggcccccatg gtgg | 14 |

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ccccatggtg gagg                                                        14

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aaggaaagca agaaaga                                                     17

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccatggtgga gg                                                          12

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
accttcggta gcgagg                                                      16

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcgagggcaa ggaaa                                                       15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggtgggtttg gctgg                                                       15

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agttgcctgg acattc                                                    16

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgtcgcttgt gccgg                                                     15

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggtctttctc cccact                                                    16

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggcacagcca cagg                                                      14

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggtagcgagg gcaa                                                      14

<210> SEQ ID NO 54
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctgctggggc tcta                                                      14

```
-continued

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aaggaaagca agaaa                                                       15

<210> SEQ ID NO 56
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ccccatggtg g                                                           11

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agtcatggcc c                                                           11

<210> SEQ ID NO 58
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
caagaaagac acc                                                         13
```